United States Patent [19]

Bettarini et al.

[11] Patent Number: 4,607,035

[45] Date of Patent: Aug. 19, 1986

[54] 1-PHENOXY(PHENYLTHIO)-4-ARYLALK-YNYLOXY-BENZENE DERIVATIVES ENDOWED WITH A JUVENILE HORMONIC AND AN ACARICIDE ACTIVITY

[75] Inventors: Franco Bettarini, Novara; Pietro Massardo, Milan; Paolo Piccardi, Milan; Franca Reggiori, Milan; Angelo Longoni, Milan, all of Italy

[73] Assignee: Montedison S.p.A., Milan, Italy

[21] Appl. No.: 516,354

[22] Filed: Jul. 22, 1983

[30] Foreign Application Priority Data

Jul. 23, 1982 [IT] Italy .............................. 22552 A/82

[51] Int. Cl.$^4$ .................... C07D 213/30; A01N 43/40

[52] U.S. Cl. .................................. 514/277; 546/339; 549/61; 549/62; 549/78; 560/18; 560/64; 560/65; 558/424

[58] Field of Search ...................... 546/339; 424/263; 514/277

[56] References Cited

U.S. PATENT DOCUMENTS

4,512,995  4/1985  Rose ................................. 514/277

Primary Examiner—Alan L. Rotman

[57] ABSTRACT

There are described 1-phenoxy(phenylthio)-4-arylalkynyloxy-benzene derivatives endowed with a juvenile hormonic activity towards insects and with an acaricide activity. The use of these compounds for controlling insects infestations in both the agrarian and civil field and the processes for preparing said compounds are described too.

6 Claims, No Drawings

1-PHENOXY(PHENYLTHIO)-4-ARYLALK-YNYLOXY-BENZENE DERIVATIVES ENDOWED WITH A JUVENILE HORMONIC AND AN ACARICIDE ACTIVITY

BACKGROUND OF THE INVENTION

"Compounds endowed with a juvenile hormonic activity" or briefly "juvenile hormones" are terms which indicate, whenever used in the present description, those compounds which, although not being natural juvenile hormones of the insects, possess nevertheless analogous characteristics thereof.

When these compounds come into contact with juvenile forms of insects such as, e.g., larvae or neanids or even embryos in the egg, they are capable of affecting the development of the insect depending on the time and on the administered dose, also causing, depending on the species, the death of the individual insect or serious malformations leading to the death or to individuals unable to reproduce.

Also in applications to adult forms, these compounds may prove to be active in preventing the insect reproduction by inhibiting the oviposition or the hatching of the eggs.

The use of compounds endowed with a juvenile hormonic activity offers considerable ecological advantages as compared with the conventional insecticides; in fact, the juvenile hormones are highly selective, wherefore they do not damage the useful species and, above all, are little toxic towards warm-blooded animals and fish.

Several compounds exerting a juvenile hormonic activity are known, such as the ones described in U.S. Pat. Nos. 4,061,683; 4,141,921 and 4,153,731 (Ciba Geigy), in British patent application No. 2,023,591 and in U.S. Pat. No. 4,126,623 (Montedison S.p.A.).

THE PRESENT INVENTION

We have now found compounds having the formula

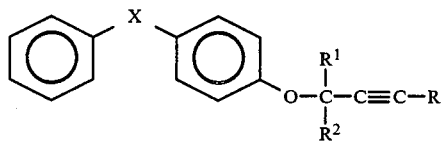

wherein:

R is a 2-furyl, 2-thienyl, pyridyl or phenyl radical, with the pyridyl or phenyl radical being optionally substituted by one or more groups selected from: alkyl $C_1$–$C_5$, haloalkyl $C_1$–$C_5$ having 1 to 3 halogen atoms, alkenyl $C_2$–$C_5$, haloalkenyl $C_2$–$C_5$ having 1 to 3 halogen atoms, alkynyl $C_2$–$C_5$, alkoxy $C_1$–$C_5$, haloalkoxy $C_1$–$C_5$ having 1 to 3 halogen atoms, alkylthio $C_1$–$C_5$, alkoxycarbonyl having 1 to 5 carbon atoms in the alkoxy moiety, alkylcarbonyl having 1 to 5 carbon atoms in the alkyl, nitro, cyano and halogen;

X is an atom of oxygen or of bivalent sulphur;

$R^1$ and $R^2$ (either like or unlike each other) are a hydrogen atom, a methyl or ethyl group.

The compounds of formula I are endowed with a juvenile hormonic activity and are suited to be employed for controlling insects infestations.

The compounds of formula I are preparable according to two alternative processes comprising reactions which are known in themselves in organic chemistry.

The choice between the two processes substantially depends on the particular compound which is to be prepared as a function of the reactivity of the corresponding intermediates in the individual reaction of each process.

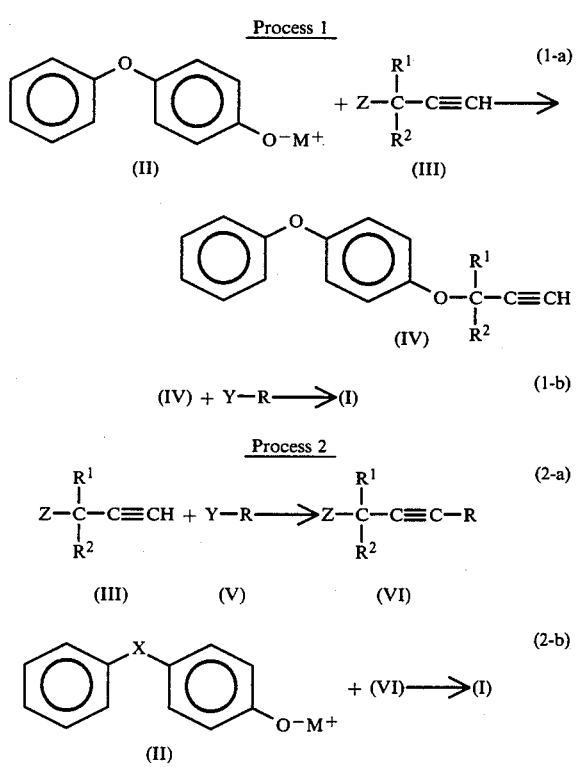

In the reactions indicated hereinabove, symbols R, $R^1$, $R^2$ and X have the same meanings specified for formula I, $M^+$ represents the cation of an alkaline metal (sodium or potassium), Z is an atom of chlorine or bromine or a tosyl group (p.toluene-sulphonate), Y is an atom of bromine or iodine.

Compound (II) is the alkaline salt of 4-phenoxy-phenol or 4-phenylthio-phenol which is generally prepared in the reaction medium from the corresponding phenol and from an alkaline base (sodium or potassium hydroxide, potassium carbonate, etc.).

The alkynes of formula III are compounds known as halides (Z=Cl, Br) or as alcohols (Z=OH); from the latter, the corresponding tosylate (Z=tosyl) being readily preparable by reaction with tosyl-chloride.

The compound of formula V (Y-R) is a haloaromatic compound, for example when Y=Br, it is 2-bromo-furan, 2-bromo-thiophene, bromo-pyridine or bromo-benzene, the latter two being optionally substituted according to what has been specified for formula I.

Reactions 1-a and 2-b are carried out by preparing, in a suitable polar solvent, the alkaline salt II (from the corresponding phenol and from an alkaline base) and by adding to the salt solution or suspension, the alkyne III or IV either as such or dissolved in a suitable solvent.

Reactions 1-b and 2-a are carried out in the presence of a nickel complex or of a palladium complex as a catalyst, according to the methodology described by L.

Cassar, J. Organometallic Chem. 93, 253 (1975) or by K. Sonogashira et al., Tetr. Lett. 50, 4467 (1975).

In particular, reaction 2-a can be advantageously carried out when the alkyne of formula III contains an alcoholic functional group (Z=OH) which, after reaction, can be readily converted into the corresponding halide or tosylate.

Some of the compounds of formula IV and in particular 1-phenoxy-4-propargyloxy-benzene and 1-phenoxy-4-(butyn-3-yloxy)-benzene have been described as juvenile hormones in U.S. Pat. No. 4,141,921. Their juvenile hormonic activity results to be remarkably lower than the one of the compounds of formula I.

As mentioned hereinbefore, the compounds of formula I are endowed with a juvenile hormonic activity.

This activity explicates even at very low doses, both versus larvae and versus insect eggs.

Among the insects against which the compounds of formula I prove to be active, there are important species of Coleoptera, Lepidoptera, Diptera, Hymenoptera, Hemiptera, Orthoptera and Siphonaptera.

An interesting collateral activity is the acaricide activity against acari eggs, this property being rather uncommon among the compounds endowed with juvenile hormonic activity.

The compounds of formula I prove furthermore to be little toxic for warm-blooded animals and fish.

Thanks to their high activity also at very low doses, to their activity spectrum and to the low toxicity, the compounds of formula I are well suited to be utilized for fighting insect infestations in both the agrarian and the civil field.

For practical uses, they are employable either as such or, preferably, as a suitable insecticide composition.

Said compositions contain, besides one or more of the compounds of formula I as an active ingredient, also a solid or liquid inert vehicle and optionally other additives which are commonly used in the formulative field, such as e.g. surfactants, wetting agents, antioxidants, suspending agents, adhesion-promoting agents, and the like.

With the compounds of formula I it is also possible to prepare compositions in the form of alimentary baits, which are useful to control certain insect species which are harmful in both the agrarian and the civil field.

Generally, the baits consist of a solid or liquid substance of alimentary origin, attractive for the insect, onto or into which the compound of formula I is added. Also the baits may contain usual additives consistent with the particular utilization.

If desirable, it is possible to add to the insecticide compositions also other compatible active substances selected—in consideration of the purpose to be achieved—amongst conventional insecticides, acaricides, fungicides, etc.

According to a usual formulative practice, the insecticide compositions may be in the form of emulsifiable concentrates, liquid concentrates, dispersions, pastes, powders, granules, wettable powders, etc.

The amount of compound of formula I to be used depends on various factors such as, e.g., the relative effectiveness of the particular compound of formula I considered, the insect species to be controlled, the type and degree of infestation, the infestation place (domestic or civil ambient, stables, agrarian cultivations, pastures, stretches of water, food-stuff, other places frequented by the man or by the animals, or the animals themselves, etc.), climatic and environmental conditions.

Generally, product amounts of from 1 to 1000 g/ha are sufficient for the uses in the agrarian, domestic or civil field For other uses, the compound amount is calculated in consideration of factors cited hereinabove.

The following examples are given to better illustrate the present invention.

EXAMPLE 1

Preparation of compound 1-phenoxy-4-[3-(2-pyridyl)-prop-2-ynyloxy]-benzene Compound No. 1 of formula

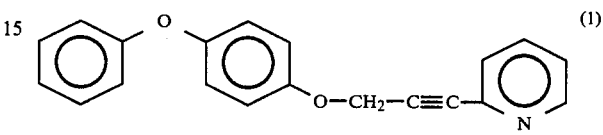

Variant a

Into a 100 ml flask equipped with a stirrer, a thermometer and a reflux condenser, maintained in a nitrogen atmosphere, there were introduced:

20 ml of dimethylformamide, 1.1 g (5 . $10^{-3}$ moles) of 1-phenoxy-4-propargyloxy-benzene (prepared in like manner as described in U.S. Pat. No. 4,141,921), 0.81 g (5 . $10^{-3}$ moles) of 2-bromo-pyridine, 0.25 g of palladium-bis-triphenylphosphine-dichloride $Pd[P(C_6H_5)_3]_2Cl_2$, 0.24 g (6 . $10^{-3}$ moles) of ground NaOH, 0.15 g of cuprous iodide CuI.

The reaction mixture was heated to 100° C. for four hours, under stirring, in a nitrogen atmosphere.

After cooling, the mixture was poured into water and extracted with ethyl ether.

The ethereal extracts were gathered and washed with water, until neutral pH, whereafter they were dried on anhydrous sodium sulphate. The solvent was then removed by evaporation under reduced pressure and the residue was purified by chromatography on a silica gel column (eluent: hexane-ethyl ether in the ratio 7:3).

0.9 g of the desired product as a crystalline solid (melting point=74° C.) were thus obtained.

Variant b

Into a 250 ml flask equipped with a stirrer, a thermometer, a reflux condenser and maintained in a nitrogen atmosphere, there were introduced:

80 ml of triethylamine, 6.16 g (27.5 . $10^{-3}$ moles) of 1-phenoxy-4-propargyloxy-benzene, 4.35 g (27.5 . $10^{-3}$ moles) of 2-bromo-pyridine, 140 mg of palladium-bis-tripenylphosphine-dichloride, 80 mg of cuprous iodide.

The reaction mixture was heated at reflux for four hours.

After cooling, 100 ml of ethyl ether were added and the resulting solid (trimethylammonium bromide) was filtered.

The solvents were eliminated under reduced pressure and the residue was purified by chromatography on an alumina column (eluent: hexane-ethyl ether in the ratio 7:3). 4.7 g of the desired product (melting point=74° C.) were thus obtained.

1H NMR (CDCl₃, TMS)

δ(ppm): 4.87 (s, 2H); 6.77–7.82 (m, 12H); 8.40–8.62 (m, 1H)

(s=singlet, m=multiplet or non-resolved complex signal).

EXAMPLE 2

Preparation of compound 1-phenoxy-4-[3-(4-methoxy-phenyl)-prop-2-ynyloxy-]-benzene [Compound No. 2] of formula

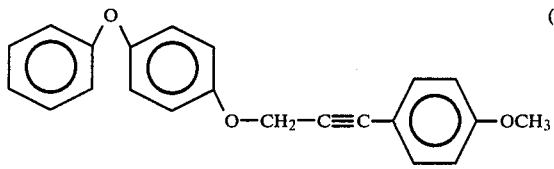

The preparation was accomplished by operating in like manner as is described in example 1, variant a, starting from 1-phenoxy-4-propargyloxy-benzene and from 4-bromo-anisole. Compound No. 2 was in the form of a white solid.

¹H-NMR (CDCl₃, TMS)

δ(ppm): 3.75 (s, 3H); 4.85 (s, 2H); 6.70–7.45 (m, 13H).

EXAMPLE 3

Preparation of compound 1-phenoxy-4-[3-(4-methyl-phenyl)-prop-2-ynyloxy]-benzene [Compound No. 3] of formula

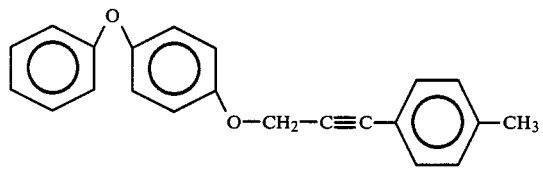

The preparation was accomplished by operating in like manner as is described in example 1, variant a, starting from 1-phenoxy-4-propargyloxy-benzene and from 4-bromo-toluene.

Compound No. 3 was in the form of a white solid.

¹H-NMR (CDCl₃, TMS)

δ(ppm): 2.30 (s, 3H); 4.80 (s, 2H); 6.78–7.42 (m, 13H).

EXAMPLE 4

Preparation of compound 1-phenoxy-4-[3-(4-nitro-phenyl)-prop-2-ynyloxy]-benzene [Compound No. 4] of formula

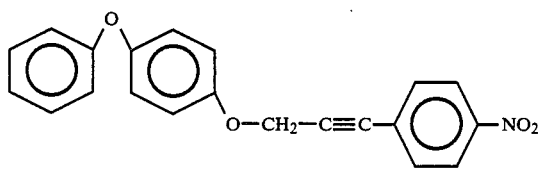

The preparation was accomplished by operating in like manner as is described in example 1, variant b, starting from 1-phenoxy-4-propargyloxy-benzene and from 4-nitro-bromobenzene.

Compound No. 4 was in the form of a crystalline solid (melting point=125° C.).

EXAMPLE 5

Preparation of compound 1-phenoxy-4-(3-phenyl-prop-2-ynyloxy)benzene [Compound No. 5] of formula

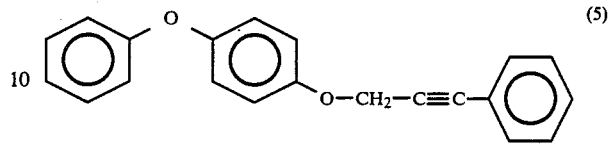

The preparation was accomplished by operating in like manner as is described in example 1 variant b starting from 1-phenoxy-4-propargyloxy-benzene and from iodobenzene. Compound No. 5 was in the liquid form at room temperature.

¹H - NMR (CDCl₃, TMS)

δ(ppm): 4.85 (s, 2H); 6.80–7.75 (m, 14H).

EXAMPLE 6

By operating according to the procedure described in Example 1, the compounds reported in the following Table 1 were prepared.

TABLE 1

Compounds of formula:[1]

| Compound No.[2] | R | R¹ | R² | X | m.p.[3] (°C.) |
|---|---|---|---|---|---|
| 1 | 2-pyridyl | H | H | O | 74 |
| 2 | 4-CH₃O—C₆H₄ | H | H | O | solid |
| 3 | 4-CH₃—C₆H₄ | H | H | O | solid |
| 4 | 4-NO₂—C₆H₄ | H | H | O | 125 |
| 5 | C₆H₅ | H | H | O | oil |
| 6 | 2-thienyl | H | H | O | oil |
| 7 | 4-CH₃CO—C₆H₄ | H | H | O | 52–3 |
| 8 | 4-CN—C₆H₄ | H | H | O | 105–7 |
| 9 | 4-CF₃—C₆H₄ | H | H | O | 73–4 |
| 10 | 4-Cl—C₆H₄ | H | H | O | 80–1 |
| 11 | 2-pyridyl | CH₃ | H | O | oil |
| 12 | 4-CH₃O—C₆H₄ | CH₃ | H | O | oil |
| 13 | 4-Br—C₆H₄ | H | H | O | 90–1 |
| 14 | 4-pyridyl | H | H | O | oil |
| 15 | 2,5-Cl₂—C₆H₃ | H | H | O | 83–4 |
| 16 | 3,5-Cl₂—C₆H₃ | H | H | O | oil |
| 17 | 3,5-Cl₂—C₆H₃ | CH₃ | H | O | oil |
| 18 | 2-(COOCH₃)—C₆H₄ | H | H | O | oil |
| 19 | C₆H₅ | H | H | S | 75 |
| 20 | C₆H₅ | CH₃ | H | S | oil |
| 21 | 2-pyridyl | H | H | S | oil |
| 22 | 2-pyridyl | CH₃ | H | S | oil |
| 23 | 4-F—C₆H₄ | H | H | O | 55–6 |
| 24 | 2-CH₃—C₆H₄ | H | H | O | 51–3 |
| 25 | 2-CH₃O—C₆H₄ | CH₃ | H | O | 48–50 |
| 26 | 4-CH₃O—C₆H₄ | H | H | S | 76–7 |
| 27 | 4-CH₃O—C₆H₄ | CH₃ | H | S | oil |
| 28 | 2-pyridyl | CH₃ | CH₃ | O | oil |
| 29 | 4-CH₃O—C₆H₄ | CH₃ | CH₃ | O | oil |
| 30 | 2-CH₃O—C₆H₄ | CH₃ | CH₃ | O | oil |
| 31 | 3-CH₃—C₆H₄ | H | H | O | oil |
| 32 | 5-Cl—2-pyridyl | CH₃ | CH₃ | O | oil |
| 33 | 5-Cl—2-pyridyl | CH₃ | H | O | oil |
| 34 | 5-Cl—2-pyridyl | H | H | O | 71–3 |
| 35 | 4-CH₃O—C₆H₄ | CH₃ | CH₃ | S | oil |
| 36 | 2-pyridyl | CH₃ | CH₃ | S | oil |
| 37 | 5-CH₃—2-pyridyl | H | H | O | 82–4 |
| 38 | 4-CH₃—2-pyridyl | H | H | O | 60–1 |

TABLE 1-continued

Compounds of formula:[1]

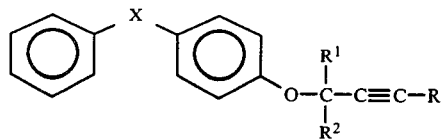

| Compound No.[2] | R | R¹ | R² | X | m.p.[3] (°C.) |
|---|---|---|---|---|---|
| 39 | 6-$CH_3$—2-pyridyl | H | H | O | oil |

Notes to Table 1
[1]The $^1H$—NMR spectroscopic data of all the compounds are consistent with the assigned structure
[2]Compounds 1 to 5 are described in examples 1 to 5 respectively.
[3]m.p. = melting point. Melting points have not been corrected. The compounds described as oil are thick oils at room temperature which, in most cases, solidify when cooled at about −10 ÷ 0° C.

EXAMPLE 7

Determination of the biological activity of the compounds of Table 1 (see Example 6).

Determination of the juvenile hormonic activity (1) *Spodoptera littoralis* (Lipidoptera) larvae 0–36 hour old larvae of the 6th age were treated by topically applying, through a microsyringe, 2 μl of an acetonic solution of the product onto the first two urosternites. As a check, another group of larvae of the same age was treated under the same conditions only with acetone. The insects were maintained at 25°±1° C. and 65±5% of relative humidity in the presence of artificial pabulum as a food and of sawdust for letting the larvae become chrysalids. The hormonal activity was expressed as the percentage, corrected according to Abbott in respect of the check, of the abnormal living and dead insects (larvae, chrysalides and adults) determined when the emergence from the cocoon of the insects not treated with the product (check) was completely concluded (about 20 days after the treatment). Compounds Nos. 1, 2 and 3 showed full activity (100%) at a dose of 200 γ/insect.

(2) *Aedes aegypti* (Diptera) larvae

Into pots containing 297 ml of spring water each, 3 ml of an acetonic solution of the Product were added and, successively, 25 larvae of the 3rd and 4th ages were introduced, whereupon the pots were closed by means of gauze. It was operated in like manner for the check by introducing the larvae into pots containing 300 ml of spring water. The samples were kept at 27° C., and to the larvae was given daily a proper food in powder.

The hormonal activity was expressed as percentage of reduction, with respect to the check, in the number of morphologically normal adults emerged from the cocoon, determined when the emergence from the cocoon of the insects not treated with the product (check) was completely concluded (about 14 days after the test beginning). Compounds Nos. 1, 2, 3, 4, 6, 8, 10, 11, 14, 16, 19, 20, 21, 33, 37, 38 and 39 exhibited a complete activity (100%) at a dose of 2 ppm.

(3) *Musca domestica* (Diptera) larvae

Into pots containing 250 g each of larval breeding pabulum, 5 ml of an acetonic solution of the product were introduced, whereafter accurately mixed. It was operated in like manner for the check, but the treatment was carried out with acetone only.

The pabulum of each pot was then infested with 100 two-day old larvae and kept at 25°±1° C. and 65±5% of relative humidity.

After 60 days the pupae present in the pabulum were collected and transferred to another pot, waiting for the emergence from the cocoon.

The hormonal activity is expressed as percentage of reduction, as compared with the check, in the number of morphologically normal adults emerged from the cocoon, determined when the emergence from the cocoon of the insects not treated with the product (check) was completely concluded (about 10 days from the test beginning). Compounds No. 1, 2, 3 and 30 exhibited a complete activity (100%) at a dose of 20 ppm.

(4) *Tribolium confusum* (Coleoptera) larvae

Into pots containing 5 g of wheat meal each, 5 ml of a acetonic solution of the product were added, whereafter it was carefully mixed. It was operated in like manner for the check, but the treatment was carried out with acetone only. After evaporation of the solvent, the wheat meal was carefully mixed once again and infested with 25 larvae of 20–22 days of age. The samples were kept at 25°±1° C. and 65±5% of relative humidity.

The hormonic activity was expressed as percentage of reduction, as compared with the check, in the number of morphologically normal adults emerged from the cocoon, determined when the emergence from the cocoon of the insects not treated with the product (check) was fully concluded (about 45 days after the test began).

Compounds Nos. 1, 2, 3, 4, 5, 6, 7, 11, 12, 21, 22, 27, 29, 31, 32, 33, 34, 35, 36 and 37 exhibited a complete activity (100%) at a dose of 200 ppm., most of them being still completely effective at 20 ppm.

Determination of the acaricide activity

*Tetranychus urticae* (Acari) eggs

Small discs (2.5 cm diameter) of bean leaves were infested with about twenty adult females/disc.

After 24 hours the mites were removed and the discs bearing the eggs were treated by immersion into a hydroacetonic dispersion (10% acetone) of the product.

It was operated in like manner for the check, but the treatment was accomplished with a hydroacetonic solution only. The treated discs were kept at 23°±1° C. and 70±5% of relative humidity.

The activity was expressed as percentage of reduction, with respect to the check, in the number of hatched eggs determined when the hatching of the eggs not treated with the product (check) was completely concluded (about 7 days after the test began).

Compounds Nos. 1, 2, 3, 4, 14, 15, 17, 19, 20, 23, 24, 25, 26, 31, 33, 36 and 38 exhibited a complete activity (100%) at a dose of 0.1%.

What we claim is:

1. A compound having the following structure

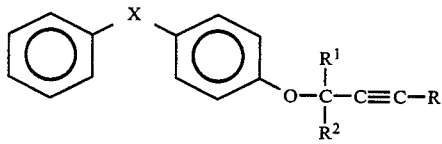

in which R is selected from the group consisting of pyridyl and pyridyl substituted by a substituent selected from the group consisting of the methyl group and chlorine, X is selected from the group consisting of oxygen and divalent sulphur, and $R^1$ and $R^2$, the same or different, are selected from the group consisting of hydrogen, methyl and ethyl.

2. A compound selected from the group consisting of
1-phenoxy-4-[3-(2-pyridyl)-prop-2-ynyl-oxy]-benzene,
1-phenoxy-4-[3-(4-methoxyphenyl)-prop-2-ynyloxy]-benzene,
1-phenoxy-4-[3-(4-methylphenyl)-prop-2-ynyloxy]-benzene,
1-phenoxy-4-[3-(4-nitrophenyl)-prop-2-ynyl-oxy]-benzene and
1-phenoxy-4-[3-(phenyl-prop-2-ynyloxy)]-benzene.

3. 1-phenoxy-4-[3-(2-pyridyl)-prop-2-ynyl-oxy]-benzene.

4. An insecticidal or acaricidal composition containing a compound of claim 2 as an active ingredient besides liquid or solid inert carriers.

5. A method of controlling infestations due to insects or acari consisting of employing on the infested area an effective amount of a compound of claim 2.

6. A method of controlling infestations due to insects or acari consisting of employing a composition containing a compound of claim 2 as active ingredient of the composition.

* * * * *